(12) United States Patent
Tyren et al.

(10) Patent No.: US 8,414,772 B2
(45) Date of Patent: Apr. 9, 2013

(54) METHOD FOR DIFFERENTIATION OF SUBSTANCES

(75) Inventors: Carl Tyren, Monaco (MC); Jarl Ahlmen, Billdal (SE)

(73) Assignee: Pacar Holding AB (SE)

( * ) Notice: Subject to any disclaimer, the term of this patent is extended or adjusted under 35 U.S.C. 154(b) by 0 days.

(21) Appl. No.: 12/743,497

(22) PCT Filed: Nov. 19, 2008

(86) PCT No.: PCT/SE2008/000651
§ 371 (c)(1),
(2), (4) Date: May 18, 2010

(87) PCT Pub. No.: WO2009/067071
PCT Pub. Date: May 28, 2009

(65) Prior Publication Data
US 2010/0276366 A1    Nov. 4, 2010

(30) Foreign Application Priority Data
Nov. 19, 2007   (SE) ...................................... 0702553

(51) Int. Cl.
- B01D 17/00 (2006.01)
- B01D 17/02 (2006.01)
- B01D 11/00 (2006.01)
- B01D 61/38 (2006.01)

(52) U.S. Cl.
USPC ............ 210/643; 210/645; 210/646; 210/767

(58) Field of Classification Search .................. 210/200, 210/201, 252, 258, 321.6, 456, 645, 646, 210/642, 643, 767, 805, 806; 422/100, 101, 422/104; 604/4.01, 5.01, 5.04, 6.09, 6.11, 604/6.16
See application file for complete search history.

(56) References Cited

U.S. PATENT DOCUMENTS

| | | |
|---|---|---|
| 4,147,621 A | 4/1979 | Giddings |
| 4,737,268 A | 4/1988 | Giddings |
| 4,894,146 A | 1/1990 | Giddings |

(Continued)

FOREIGN PATENT DOCUMENTS

WO    2006124431 A2    11/2006

OTHER PUBLICATIONS

Leonard et al. "Dialysis Without Membranes: How and Why?", Blood Purification 2004, vol. 22, p. 92-100.

(Continued)

Primary Examiner — John Kim
(74) Attorney, Agent, or Firm — Brooks Kushman P.C.

(57) ABSTRACT

A method and a device for differentiation of substances in a body fluid, such as blood, plasma or used peritoneal dialysis fluid, for example for hemodialysis. The device has a compartment having several inlets for entering a body fluid, a transition fluid and a diffusion fluid for flowing parallel with each other in laminar flow layers with substantially equal flow velocities. The transition fluid layer is interposed between the body fluid layer and the diffusion fluid layer. The compartment further has a first outlet for removing the body fluid and the transition fluid and a second outlet for removing the diffusion fluid. Pumps are arranged for controlling the flow velocities so that a marker substance, such as albumin, will not diffuse from the body fluid layer across the transition layer, during the passage of the body fluid from the inlet to the outlet of the compartment.

6 Claims, 7 Drawing Sheets

U.S. PATENT DOCUMENTS

| | | | |
|---|---|---|---|
| 5,039,426 | A | 8/1991 | Giddings |
| 5,716,852 | A | 2/1998 | Yager et al. |
| 6,136,171 | A | 10/2000 | Frazier et al. |
| 7,041,208 | B2 | 5/2006 | Staats |
| 7,404,490 | B2 | 7/2008 | Kennedy et al. |
| 7,850,633 | B2 * | 12/2010 | Leonard et al. ............... 604/5.04 |

OTHER PUBLICATIONS

Narayanan et al. "A Microfabricated Electrical SPLITT System", Lab Chip 2006, vol. 6, p. 105-114.

Gale et a. "Cyclical Electrical Field Flow Fractionation", Electrophoresis 2005, vol. 26, p. 1623-1632.

Sant et al. "Geometric Scaling Effects of Instrumental Plate Height in Field Flow Fractionation", Journal of Chromatography A 2006, vol. 1104, p. 282-290.

Ursell "The Diffusion Equation A Multi-Dimensional Tutorial" Department of Applied Physics, California Institute of Technology Pasadena CA, Oct. 2007, 12 Pages.

Leonard et al. "Measurement of Diffusion in Flowing Complex Fluids", Colloids Surf A Physicochem. Eng. Asp. 5 Pages, (2006).

Crews et al. Product Differentiation During Continuous-Flow Thermal Gradient RCP, Lab on A Chip 2008, vol. 8, p. 919-924.

Gale et al. "A Micromachined Electrical Field-Flow Fractionation (μ-EFFF) System", IEEE Transactions on Biomedical Engineering Dec. 1998, vol. 45, No. 12, p. 1459-1469.

Kantak et al. "Microfabricated Cyclical Electrical Field Flow Fractionation", Department of Mechanical Engineering, University of Utah, Salt Lake City, Ut 84112, 4 Pages.

Narayanan "Characterization of a Microfabricated Electrical Splitt System", A Thesis Submitted to the Faculty of The University of Utah in Partial Fulfillment of the Requirements for the Degree of Master of Science, Department of Mechanical Engineering The University of Utah Dec. 2004, 109 Pages.

Kaazempur-Mofrad et al. "A MEMS-Based Renal Replacement System", Solid-State Sensor, Actuator and Microsystems Workshop Hilton Head Island, South Carolina Jun. 6-10, 2004, p. 67-70.

* cited by examiner

METHOD FOR DIFFERENTIATION OF SUBSTANCES

AREA OF INVENTION

The present invention relates to a method and device for differentiation of substances in a liquid, such as body fluids, for example blood, plasma or peritoneal dialysis fluid. More specifically, the method and device relate to selective removal of substances in connection with a medical treatment such as dialysis, for example blood dialysis or peritoneal dialysis.

BACKGROUND OF INVENTION

The methods used today, and since the advent of dialysis some 50 years ago, in relation to kidney failure all relies on methods using semipermeable membranes.

While for example blood dialysis may eliminate waste products from blood, they may at the same time, unfortunately, eliminate vital to health, non-waste substances from blood. Examples of substances that should not be eliminated are albumin and some immunoglobulins.

There are many toxic substances that are poorly removed by current dialysis methods. These substances may cause uremic conditions in patients with renal failure causing suffering and illness for these patients.

As an example, the following substances are poorly removed by most known dialysis techniques: p-cresol; homocysteine; AGE (advanced glycation end products), and hippouric acid. These toxins are at least partly protein-bound making their removal difficult with conventional dialysis procedures.

Other toxic substances found in the biological system of a renal failure patient are even un-known and are still to be identified. The EUTox (European Uremic Toxin Work Group) has found that middle molecular weight substances may be strongly toxic and may be responsible for uremic conditions. Middle molecular weight substances are normally poorly removed by conventional blood dialysis.

EUTox has so far assembled the following list of middle molecular weight substances: Adrenomerullin; Atrial natriuretic peptide; β2-microglobulin; β-endorphin; cholecystokinin; clara cell protein; complement factor D; cystatin C; degranulation inhibitor protein; delta sleep-inducing peptide; endothelin; hyaluronic acid; interleukin-1α; interleukin-6; κ-1 g light chain; λ-1 g light chain; leptin; methionine-enkephaline; neuropeptide Y; parathyroid hormone; retinol-binding protein; tumor necrosis factor-α, etc.

A further problem with conventional, membrane-based dialysis is that albumin and other proteins may adhere to the surface of the membrane, which results in blocking of the pores of the membrane, resulting in an impaired dialysis process. In addition, albumin is lost, which should be prevented, since dialysis patients in general have low concentration of albumin in blood.

Many of these problems can be attributed to the use of a membrane, which is responsive for the selection of substances to be separated from the body fluid. Thus, there is a need in the art for a method and a device, which is at least partly not based on the use of membranes.

SUMMARY OF INVENTION

Accordingly, an object of the present invention is to mitigate, alleviate or eliminate one or more of the above-identified deficiencies and disadvantages singly or in any combination.

In an aspect, there is provided a method for differentiation of substances in a body fluid, comprising entering the body fluid, a transition fluid and a diffusion fluid via inlets into a compartment for flowing parallel with each other in laminar flow layers with substantially equal flow velocities, whereby the transition fluid layer is interposed between the body fluid layer and the diffusion fluid layer; removing the body fluid and at least a portion of the transition fluid via a first outlet and removing at least the diffusion fluid via a second outlet from the compartment; adjusting the flow velocities so that a marker substance will not diffuse across the transition layer, during the passage from an inlet to an outlet of the compartment.

The marker substance may be albumin. Substances in the body fluid having a larger diffusion velocity than the marker substance may diffuse into the diffusion fluid. The transition fluid and the diffusion fluid may be the same fluid, such as dialysis liquid for hemodialysis. The transition fluid may be sterile or substantially sterile.

In another aspect there is provided a device for differentiation of substances in a body fluid, comprising a compartment having several inlets for entering the body fluid, a transition fluid and a diffusion fluid for flowing parallel with each other in laminar flow layers with substantially equal flow velocities, whereby the transition fluid layer is interposed between the body fluid layer and the diffusion fluid layer; the compartment further comprising a first outlet for removing the body fluid and at least a portion of the transition fluid and a second outlet for removing at least the diffusion fluid; a flow unit for adjusting the flow velocities so that a marker substance will not diffuse across the transition layer, during the passage from an inlet to an outlet of the compartment.

In an embodiment, the sum of the fluid flow rate of the body fluid and the fluid flow rate of the transition fluid may be equal to the fluid flow rate of the first outlet. Alternatively, the fluid flow rate of the body fluid may be larger than the fluid flow rate of the first outlet.

The body fluid may be blood, plasma obtained from a blood filter as a filtrate, or peritoneal dialysis fluid obtained from the peritoneal cavity.

BRIEF DESCRIPTION OF THE DRAWINGS

Further objects, features and advantages of the invention will appear from the following detailed description of the invention with reference to embodiments shown on the drawings, in which.

DETAILED DESCRIPTION OF EMBODIMENTS

Figure 1:
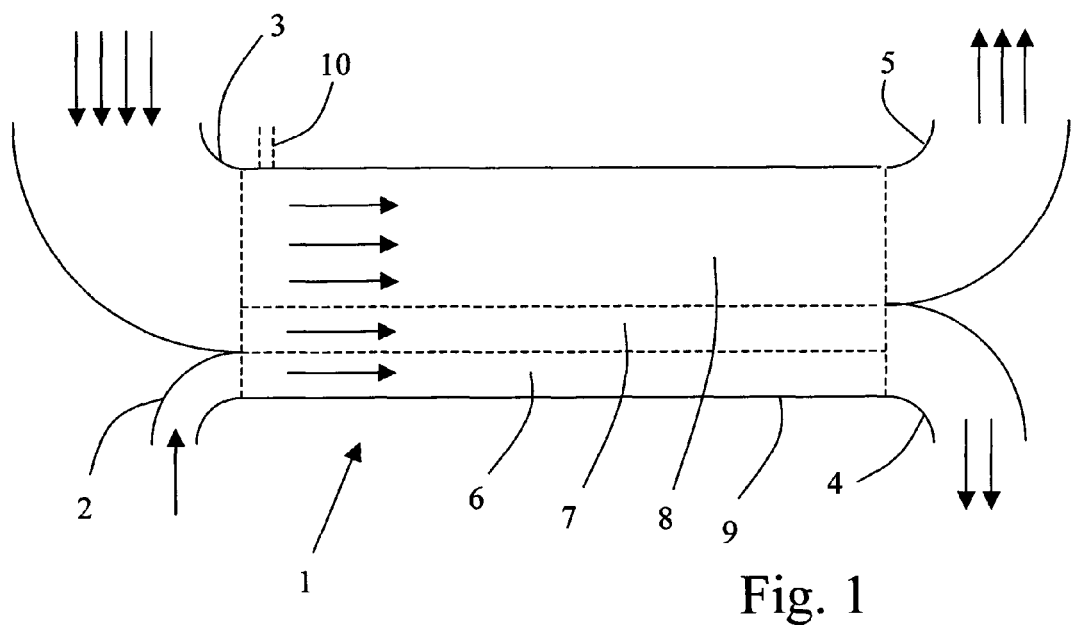
FIG. 1 is a schematic cross-sectional view of a diffusion compartment system according to an embodiment of the invention.

Below, several embodiments of the invention will be described with references to the drawings. These embodiments are described in illustrating purpose in order to enable a skilled person to carry out the invention and to disclose the best mode. However, such embodiments do not limit the invention. Moreover, other combinations of the different features are possible within the scope of the invention.

A problem of the present dialysis techniques used as renal replacement therapy is a lack of selectivity. Many of the most toxic substances are not removed by the therapy while a number of valuable substances that should not be removed are in fact removed. All dialysis machines on the market today rely on membrane technology where pore size of the membrane is the discriminating factor for what is removed.

In the dialysis techniques used today, in principle, blood is removed from the body into an extracorporeal circuit comprising a dialyzer. The dialyzer is divided into two compartments by a semipermeable membrane. Blood is circulated in a first compartment while in a second compartment, a separately prepared dialysis liquid is circulated. The blood and the dialysis liquid are in fluid contact with each other via pores in the membrane. The size of the pores is selected to be smaller than the effective size of an albumin molecule, which has a radius of about 3.5 nm and a molecular weight of about 69000 Dalton.

There are today mainly two methods of dialysis, a method based on diffusion over the membrane, and a method based on filtration by the membrane.

In the diffusion method, substances or molecules from blood pass the membrane pores driven by diffusion forces based on concentration differences over the membrane between the blood and the dialysis fluid. The dialysis fluid has a composition of specific electrolytes, such as sodium, potassium, calcium, magnesium etc, which means that these components do not diffuse out of the blood, unless the concentration in the blood is larger than in the dialysis fluid. In addition, the dialysis fluid comprises bicarbonate, which diffuses into the blood. This method is effective in removing urea, which is a marker molecule for small molecules, and other small molecules having high or moderately high concentrations. However, the diffusion method does not effectively remove middle molecules of low concentration, such as $\beta$2-microglobulin, which is a marker molecule for middle molecules. This failure of removing middle molecules is i.a. due to the low concentrations of such middle molecules and cannot be improved by increasing the pore size of the membrane.

In the filtration method, the blood is filtered by the membrane and the portion passing the membrane, the filtrate, is discarded. A replacement fluid, having substantially the same composition as mentioned above, is added to the retentate, which is returned to the body. The addition can be via post-dilution or predilution. This method is effective also in removing middle molecules such as $\beta$2-microglobulin, because of the convectional flow. However, because of the statistic distribution of the pore sizes, it is difficult to manufacture filters, which retain albumin while passing $\beta$2-microglobulin. The albumin molecule is relatively oblong and will pass a pore having a diameter of about 5 nm, while other proteins may have a more circular configuration. Thus, the filtration method may suffer from a relatively high albumin loss. In addition, a large amount of replacement fluid is required.

In addition, there is today a dialysis method called peritoneal dialysis, in which no man-made membrane is used. Instead, the peritoneal membrane of the patient is used as the selective membrane. A peritoneal dialysis fluid is installed in the peritoneal cavity of the patient. The fluid has a specific composition, which results in that substances diffuse over the peritoneal membrane from blood to the peritoneal dialysis fluid. The peritoneal dialysis fluid is replaced periodically, or more or less continually.

Embodiments of the present invention provide removal of substances from a body fluid, such as blood or plasma, without the use of man-made membranes.

It is noted, that in diffusion dialysis, the dialysis fluid flows in a counter-current flow in relation to the blood at respective side of the membrane in the dialyzer, which maximize the diffusion forces.

However, if the dialysis fluid and the body fluid are passed in the same direction and with the same flow velocity, the inventor found that the membrane could be removed, if certain criteria are fulfilled.

1) The flow should be laminar. This results in that the flows of body fluid and dialysis fluid do not substantially mix with each other.

2) A transition layer is formed between the body fluid and the dialysis fluid as explained below. The transition layer may be looked at like a membrane, but without the drawbacks, which plague the man-made membrane.

The body fluid and the dialysis fluid are in contact with each other via the transition layer, whereby concentration differences between the two fluids result in diffusion forces on the molecules. Thus, the individual molecules would diffuse from one fluid flow to the other fluid flow via the transition layer, in either direction.

For example, the body fluid, such as blood, may comprise a high concentration of urea and the dialysis fluid may comprise no urea. Thus, urea molecules will diffuse from the body fluid to the dialysis fluid. The dialysis fluid may comprise a high concentration of bicarbonate and the blood may have a lower concentration of bicarbonate, resulting in a diffusion of bicarbonate into the body fluid.

The diffusion velocity for a molecule is proportional to the concentration (difference) and inversely proportional to the radius of the molecule. Thus, albumin will diffuse much slower than urea, because of the size difference. This fact is used in the present invention. The body fluid and the dialysis fluid are in contact with each other via the transition layer for a short time period, during which albumin and other molecules having low diffusion velocity will not diffuse through the transition layer, while other molecules having a higher diffusion velocity will diffuse out of the body fluid via the transition layer to the dialysis fluid, or vice versa, as explained in more detail below.

FIG. 1 is a cross-sectional view of a diffusion unit used in the present invention. The diffusion unit is in principle a rectangular compartment having a length and a width and a height. In the embodiment shown in FIG. 1, the height dimension is increased many times for explanation reasons. An example of the dimensions may be: a length of 100 mm, a width of 20 mm and a height of 0.20 mm. Other examples are: a length of 200 mm, a width of 10 mm and a height of 0.225 mm; a length of 80 mm, a width of 10 mm and a height of 0.15 mm The diffusion unit 1 comprises two inlets 2, 3 shown to the left and two outlets 4, 5 shown to the right. The first inlet 2 comprises the body fluid, which in the embodiment shown in FIG. 1 has a flow rate of 1 ml/min. The second inlet 3 comprises a dialysis fluid having a flow rate of 4 ml/min. The first outlet 4 comprises the body fluid and a portion of the dialysis fluid. The second outlet 5 comprises the rest of the dialysis fluid.

As is evident from FIG. 1, there is formed a first body fluid layer 6 at the bottom of the compartment 1, including all molecules of the body fluid. Above the first layer, there is formed a second layer 7, which is the above-mentioned transition layer, into which molecules from the body fluid may diffuse. Above the second transition layer there is formed a third diffusion layer 8 into which the molecules of the body fluid may further diffuse.

The horizontal flow velocities of the different flows are equal. Because the flows are laminar, there is a minimum of mixing of the flows in the vertical direction.

However, molecules in the body fluid having a higher concentration in the body fluid than in the dialysis fluid will diffuse from the first layer into the second layer and further to the third layer. All molecules that diffuse into the third layer are removed by the flow out of outlet 5, while molecules that only diffuse to the second transition layer are still maintained in the flow out of outlet 4. This fact can be used for size selection based on the diffusion velocity.

Suppose that albumin molecules should be maintained in the flow of outlet 4. Then, the length of the compartment and the flow velocities are selected so that the albumin molecule may not pass beyond the second transition layer 7 into the third layer 8, while molecules having a larger diffusion velocity will pass out into the third layer.

The distance of diffusion, d, is proportional to the square root of the diffusion constant D. The diffusion constant D is proportional to the concentration, c, and inverse proportional to the effective radius, r, of the molecule. If the distance d that the albumin molecule will diffuse during the time at which the two fluids are in contact with each other over the length of the compartment 1 is set to the thickness of the second layer 6, other molecules of the body fluid would have a relative diffusion distance, d, according to the following table:

| Molecule | Concentration mmol/liter | d, relative diffusion distance |
|---|---|---|
| albumin | 0.59 | 1 |
| sodium | 135 | 88 |
| bicarbonate | 25 | 30 |
| potassium | 4 | 13 |
| urea | 3 | 10 |
| calcium | 2.5 | 8,6 |
| glucose | 4 | 8.4 |
| creatinine (100 µM) | 0.1 | 1.6 |
| beta-2-microglobuline | 0.0026 | 0.13 |
| parathyroid-hormone | 0.000015 | 0.02 |

As the table indicates, most of the electrolytes, such as sodium and potassium, have a relative diffusion distance, d, with is at least 10 times larger than albumin. Such electrolytes will be fully distributed over the compartment and have the same concentration at the two outlet flows 4, 5.

Other substances, such as beta-2-microglobulin, have a diffusion distance, which is much lower than albumin and will be retained in the first outlet flow 4.

If it is presumed that the diffusion velocity for albumin is such that albumin diffuses about 10 µm over a period of about 5 seconds, we now have the tools for setting up a process according to the first embodiment. The actual diffusion velocity of albumin depends on a number of factors, such as temperature, viscosity of the fluid, etc. Thus, the albumin diffusion velocity should be measured for each patient and for each treatment occasion, as indicated below. For the description below, the above-mentioned diffusion velocity is taken as an example.

If the compartment should be used for hemodialysis, the following conditions may be used. As the first fluid flow passing through inlet 3, whole blood is used. In addition to those substances mentioned above, whole blood comprises blood cells and other particles having a size, which is substantially larger than albumin, and thus a diffusion coefficient, which is much lower than albumin. Such particles will be retained in the first body fluid layer and the second transition layer. In addition, whole blood comprises several hormones, enzymes and proteins, having much lower concentrations than albumin and diffusion velocities much lower than albumin.

The second transition layer 7 should be about the size mentioned above for albumin diffusion during 5 seconds, i.e. about 10 µm.

The first layer should be of approximately the same size, otherwise molecules far away from the second transition layer may take too long time to diffuse to the boundary between the second transition layer and the third layer, making the process less efficient. However, the first layer should have a height, which is larger than the transition layer, because the blood is diluted by the flow volume of the transition layer. Such dilution of the blood must be reversed in a later or previous step, see further below. In the present embodiment, the height of the first layer is double that of the second layer, i.e. 20 µm.

The third layer is dimensioned as large as possible, in order to remove the alleged toxic substances to a large extent. However, if urea is used as a marker molecule, it is no use to have the height of the third layer larger than about 10 times the second layer. The larger the third layer is, the more dialysis fluid is consumed. In the present embodiment, a height of 70 µm is used.

The length of the compartment 1 is 100 mm and the width is 10 mm. Thus, the flow rate of the sum of the blood flow and dialysis fluid flow should be:

$$T=100 \text{ mm} * 10 \text{ mm} * 0.1 \text{ mm}/5 \text{ sec} = 20 \text{ mm}^3 \text{ per sec} = 1.2 \text{ ml/min}.$$

The flow rate of blood should be 0.24 ml/min and the inlet flow rate of dialysis fluid should be 0.96 ml/min. The outlet flow rate through outlet 4 is 0.36 ml/min and the outlet flow rate of outlet 5 is 0.84 ml/min. The flow velocity of all fluid flows is 0.02 m/sec. This would secure that the flow is laminar.

The removal of urea and similar molecules, which are completely diffused over the outlet flows, would be 80%. Thus, if the inlet urea concentration is 20 mM, the outlet concentration would be 4 mM, since the urea is diluted by 1:5.

Since an outlet flow of 0.84 ml/min is removed, the removal rate of urea would be about 3.36 nmol/min.

If 500 compartments are operated in parallel giving a blood flow rate of 120 ml/min, the removal rate would be 1.68 mmol/min and about 400 mmol over 4 hours. In this case, the dialysis flow rate would be 480 ml/min, which is close to that used in conventional dialysis.

Figure 2:
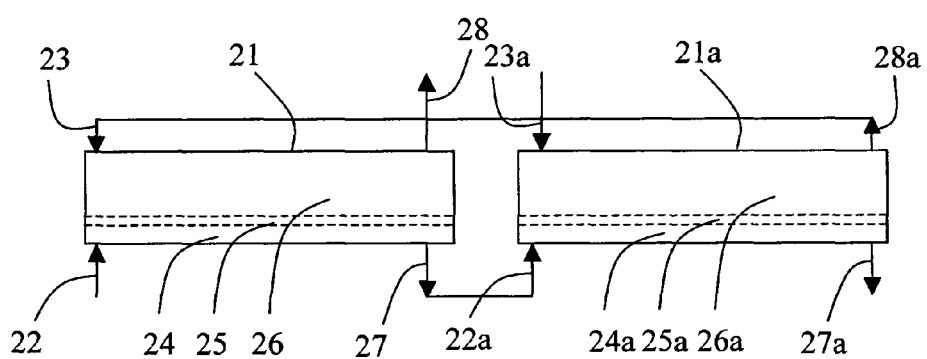
FIG. 2 is a schematic cross-sectional view of a two diffusion compartment systems according to FIG. 1 and connected in series.

A further reduction may be obtained by connecting a second compartment in series with the first compartment. In this case, the same dialysis fluid can be used twice, first in the last compartment and then in the first compartment, as shown in FIG. 2. Alternatively, separate, fresh dialysis fluids may be used.

In the embodiment according to FIG. 2, blood is entered at a first inlet 22 of a first diffusion compartment 21, forming a first blood layer 24. Dialysis fluid is entered at a second inlet 23 and forms a second transition layer 25 and a diffusion layer 26. Fluid from the blood layer 24 and fluid from the transition layer 25 exits the first compartment 21 via a first outlet 27. The fluid from the diffusion layer 26 exits the first compartment via a second outlet 28. The fluid from the second outlet 28 is discarded. The fluid from the first outlet 27 is entered into a first inlet 22a of the second compartment 21a. Fresh dialysis fluid is entered via a second inlet 23a. The fluid from the blood layer 24a and fluid from the transition layer 25a exits the second compartment 21a via a first outlet 27a and is returned to the patient. The diffusion fluid exits the second compartment 21a via a second outlet 28a and is delivered to the first compartment for reuse, in a partly counterflow configuration. If the blood layers 24, 24a are 20 µm, the transition layers 25, 25a are 10 µm and the diffusion layers 26, 26a are 30 µm, and if the urea concentration in the blood entering inlet 22 is 15 mM, then the urea concentration in the first outlet 27 from the first compartment would be 10 mM and the urea concentration in the first outlet 27a from the second compartment would be 5 mM. The urea concentration at the second inlet 23a of the second compartment 21a would be 0 mM and the urea concentration from the second outlet 28a would be 5 mM, the urea concentration at the inlet 23 of the first compartment would be 5 mM and the urea concentration at the second outlet 28 from the first compartment would be 10 mM, which is discarded. In this way, more urea is removed per dialysis volume or volume of diffusion fluid.

Since the blood is diluted by 50% in the first compartment (inlet flow is 0.24 ml/min and outlet flow is 0.36 ml/min), fluid should be removed from the blood before being returned to the patient. This can be done in any manner previously known, such as by ultrafiltration, reverse osmosis or mechanical or electrical means. If ultrafiltration is used, further urea will be removed in the ultrafiltrate, see further below.

In the embodiment according to FIG. 1, the blood is flowing adjacent a lower surface 9 of the compartment. Thus, albumin and other proteins will adhere to this surface. When the surface has been covered by proteins, no further proteins will accumulate. However, a small amount of albumin is lost by this covering process.

The blood will flow adjacent the lower surface 9, which means that the flow velocity close to the surface will be lower because of the viscosity. This slower velocity may result in that albumin will diffuse over the second transition layer to the third layer. However, the compartment should be operated at a flow rate in which the loss of albumin is a minimum. Since the concentration of albumin is different for different patients, the flow rate should be adjusted specifically for each patient. This, can be done at each treatment or at less frequent intervals for each patient, for example once per month. The flow rate is adjusted so that a minimum of albumin is detected at the outlet.

Retention of albumin may be improved by exposing the compartment for an electric field having a positive polarity at the lower surface. Albumin has a negative charge and will be deflected downwards.

In addition, the arrangement of the compartment as shown in FIG. 1 with the dialysis flow at the bottom, will result in that gravitation forces acting downwards will counteract the diffusion of the large molecules in the upwards direction.

Alternatively, it may in some cases be desired to arrange the compartment in the vertical direction instead of the horizontal direction shown in FIG. 1, or still alternatively with the body fluid in the upper part of the compartment opposite as shown in FIG. 1.

As appears from the table above, the removal of creatinine is smaller than the removal rate of urea. Thus, the calculations of how many compartments that should be used in series and/or in parallel may be based on the removal rate of creatinine rather than on the removal rate of urea.

Since the diffusion of creatinine is smaller than the diffusion of urea, it may be advantageous to use several serial stages and to have a smaller fraction of dialysis fluid in each stage. In a third embodiment, the dimensions for the first and second layers are the same, but the third layer is only 20 µm. Then, the urea and/or creatinine molecules would be diluted by about 2.5 times. Then, a second compartment in series would be required.

Figure 2A:
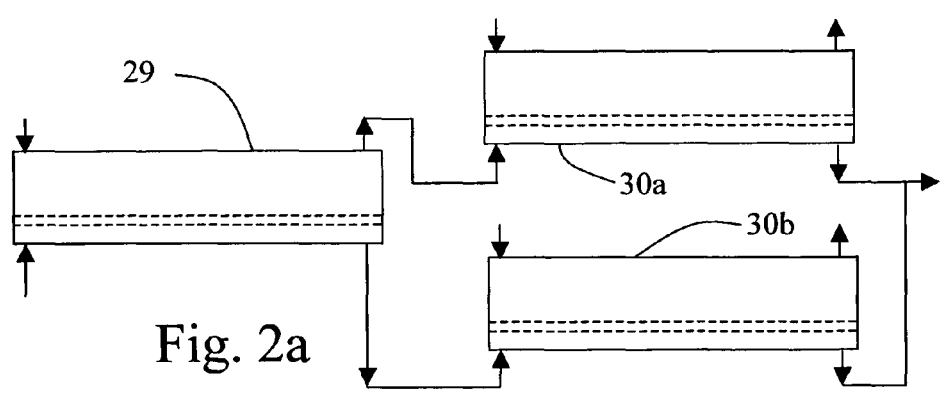
FIG. 2a is a schematic cross-sectional view of a three diffusion compartment systems according to FIG. 1 and connected in series.
Figure 6:
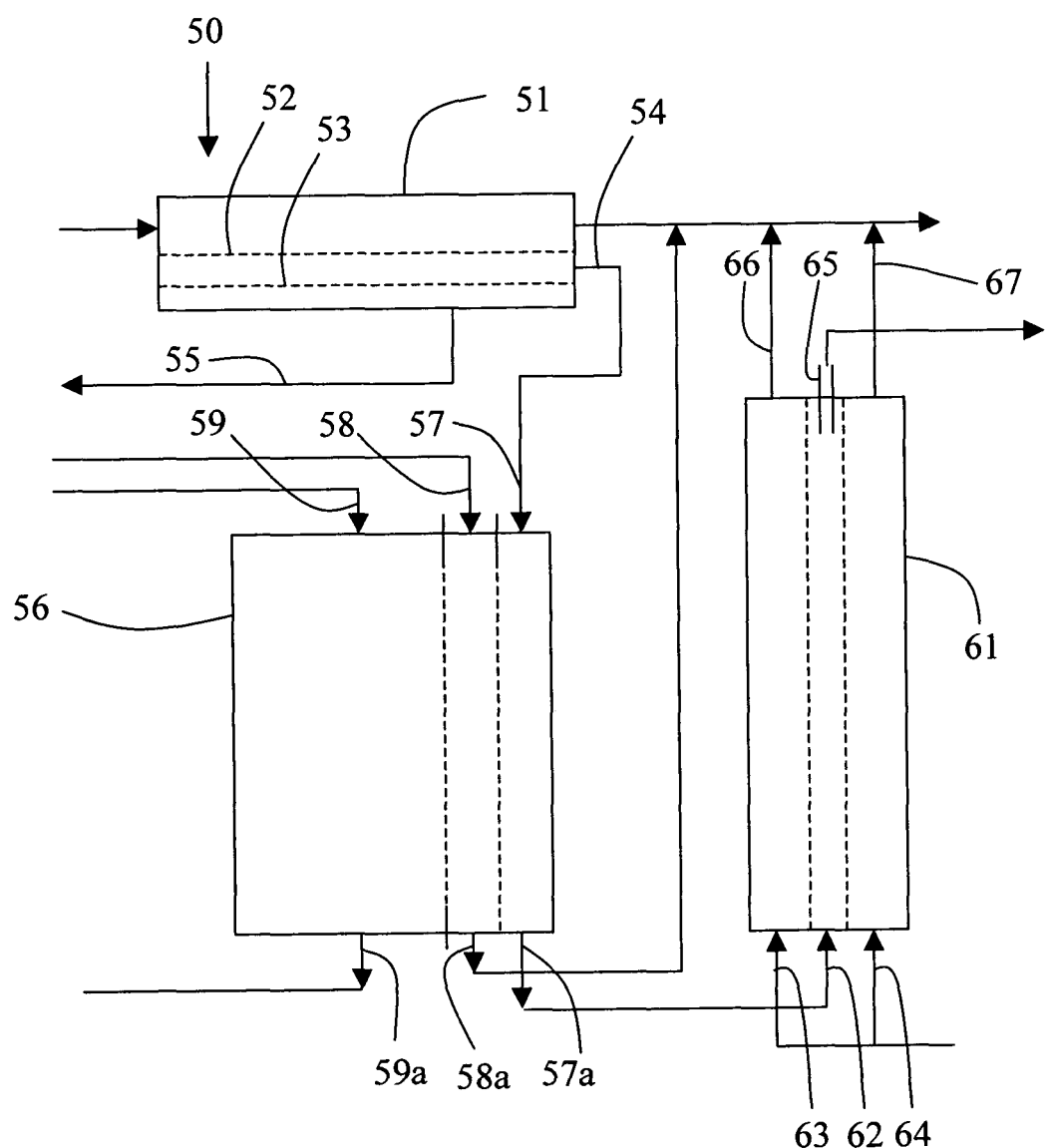
FIG. 6 is a schematic cross-sectional view of a diafiltration system according to a further embodiment of the invention, showing the principle of a reverse diffusion compartment system.

FIG. 2a discloses an embodiment comprising a first compartment 29 which is arranged so that molecules with a diffusion distance smaller than beta-2-microglobulin would be retained in the outlet flow from the lower outlet, which is passed further on to a second compartment 30b, for further separation based on another marker molecule. The outlet from the upper outlet is passed further on to a third compartment 30a for further separation based on other marker molecules. In this way, a desired separation based on the diffusion distance of different marker molecules may be obtained. Further differentiation can be obtained by having several outlets, for example as shown in FIG. 6.

In the embodiments described above, albumin is used as a marker molecule or substance for determining the size of the transition layer and the flow conditions. Another marker substance may be used as well, such as creatinine. A marker molecule may be added to the diffusion fluid layer and the absence or presence of the marker molecule in the outlet flow may be detected. For example, glucose may be added in a separate port 10 at the upper, left part of the compartment. The addition of the marker substance may be only at the setup of the system and the flow velocity can be determined during such addition.

Figure 3:
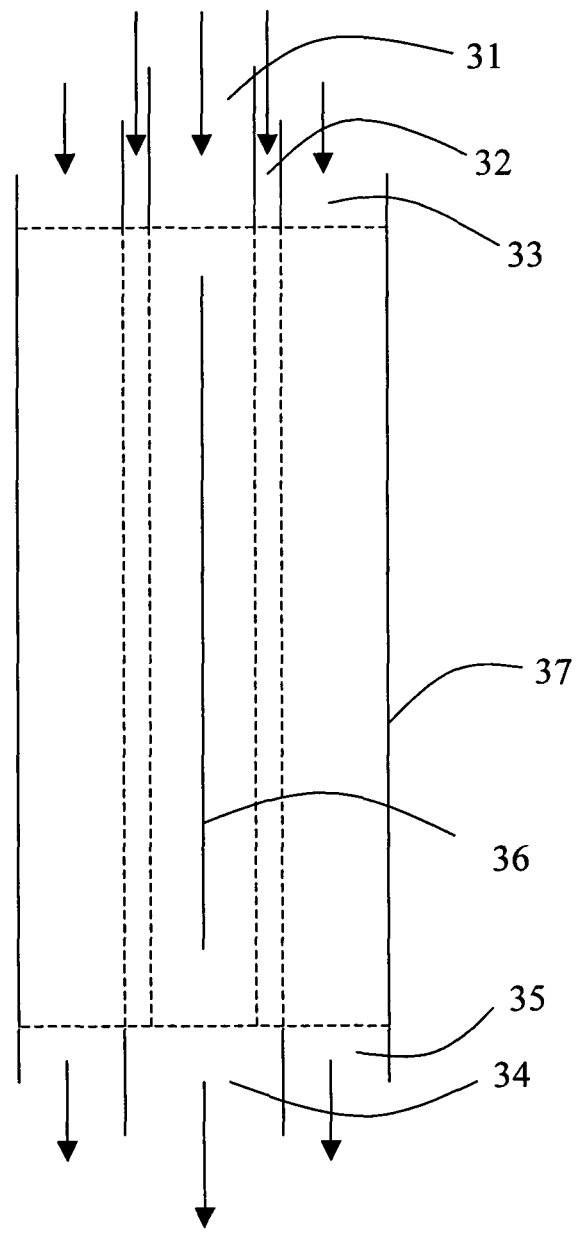
FIG. 3 is a schematic cross-sectional view of another embodiment of a diffusion compartment system.

In order to increase the diffusion of creatinine, urea and other small size molecules and at the same time to retain albumin, the body fluid may be arranged in the middle surrounded by separation layers at both sides, as shown in FIG. 3.

In the embodiment of FIG. 3, the compartment is arranged vertically, so that the gravity forces do not substantially influence upon the diffusion. The body fluid is introduced in a first inlet 31 at the top and center of the compartment. A transition fluid is introduced into a second inlet 32 arranged at each side of the first inlet 31. A dialysis fluid is introduced into a third inlet 33 arranged at each side of the second inlet. The body fluid is removed from the compartment at a first outlet 34 at the bottom center and the dialysis fluid is removed from the compartment at a second outlet 35 arranged at each side of the first outlet. The dimension may be 40 µm for the first inlet 31, 10 µm for each second inlet 32, and 40 µm for each third inlet 33. The first outlet may be 60 µm and each second outlet 40 µm. The first inlet flow may be 0.48 ml/min, the transition fluid inlet flow would be 0.12 ml/min at each side, and the dialysis fluid flow would be about 0.48 ml/min at each side. The first outlet flow would be 0.72 ml/min and the second outlet flow would be 0.48 ml/min at each side. The total sum of the flows would be 1.68 ml/min.

A separate transition fluid is delivered to the second inlets 32. Such transition fluid may be sterile fluid, such as sterile water. In this way, a sterile zone may be formed by the transition layer preventing any bacteria, virus or larger particle to pass the transition layer into the body fluid, such as blood. In this manner, the dialysis fluid may not be required to be sterile, but may be normal dialysis fluid of the same quality as accepted for normal membrane dialysis. Vice versa, any viruses in the body fluid may not pass into the dialysis fluid.

If the sterile fluid is pure water, with no electrolytes, ions and substances, the substances present in the dialysis fluid and in the body fluid will diffuse into the sterile pure water from both sides, so that after a short while, the concentration of the substances having a large diffusion coefficient, will be the same in the three different fluids. Large molecules and molecules having a low concentration in the body fluid, will pass straight downwards to the outlet 34, without passing the transition layer.

By this arrangement, molecules having a low diffusion coefficient, like creatinine will be able to diffuse through two surfaces, which means that the removal will be larger compared to the first embodiment of FIG. 1.

When a separate inlet for the transition fluid is used, the outlet 34 dimension does not need to be the sum of the inlet dimensions 31 and 32, but can be smaller or larger. Thus, the outlet 34 can be for example between 40 µm and 80 µm. However, the size of the outlet 34 in relation to the size of the inlet 31 decides the selection of molecules.

In another embodiment, the outlet 34 can be smaller than 40 µm, see further below.

The geometry may be plane as shown in FIG. 1 and FIG. 3. However, the geometry in FIG. 3 may as well be circular symmetrical, so that the first inlet 31 is cylindrical, the second inlet 32 is a concentric cylinder outside the first inlet 31 and the third inlet 33 is a further concentric cylinder outside the second inlet 32.

Figure 4:
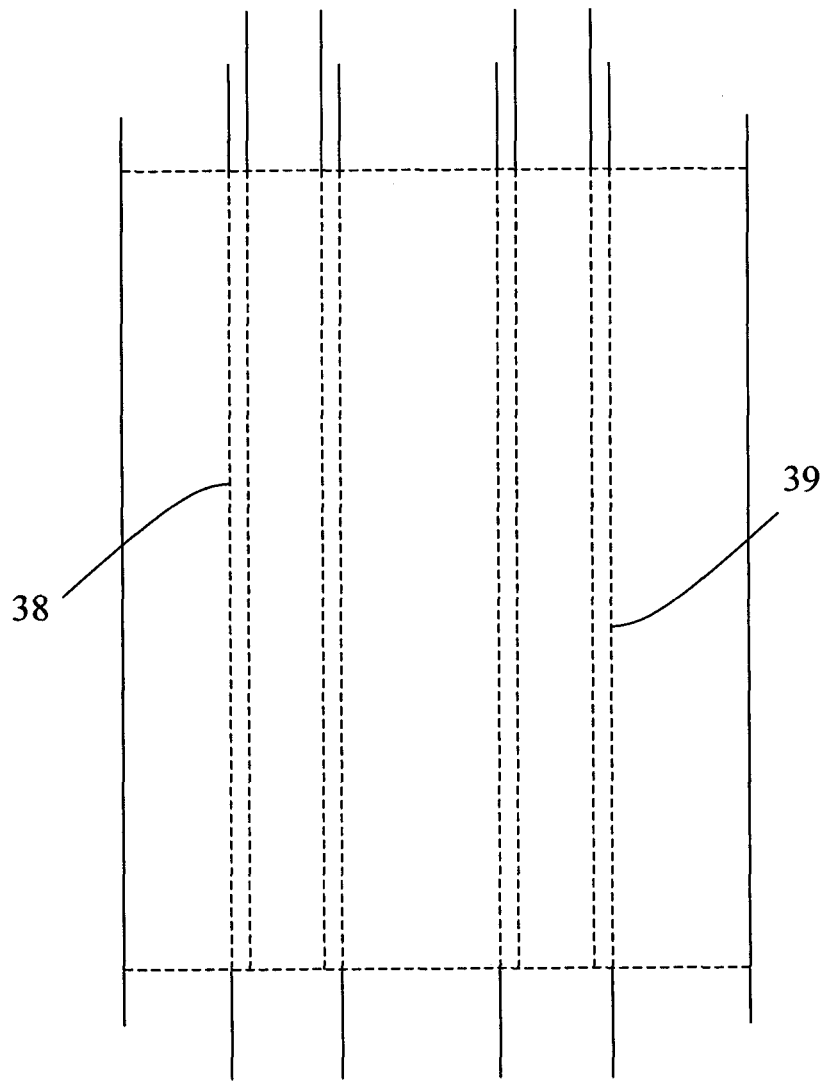
FIG. 4 is a schematic cross-sectional view of the embodiment according to FIG. 3 and having two units connected in parallel.

If the body fluid flow is cylindrical, two cylindrical fluid flows 38, 39 may be arranged beside each other as shown in FIG. 4. Three or many flows may be arranged beside each other, in a manner similar to a fiber dialysator. Thus, several tens of cylindrical flows may be arranged beside each other. The flow velocity of each flow should be equal, so that the flows are laminar and do not mix with each other.

The same is true for plane flows. Several plane flows may be arranged in a stack one above the other similar to a plate dialyzer. Several body fluid flows may be arranged beside each other with a transition layer and a diffusion layer there between.

The number of parallel flows without a supporting structure may be limited by the fact that the fluid flows should not mix with each other. By arranging several flows in parallel, the device may be sensitive to movements of any kind, including vibrations.

As described above, an electric field may be used to retain negatively charged molecules like albumin in the center flow. A central metallic rod 36 may be arranged in the center of the body fluid flow and the outer surface 37 of the compartment may be metallic. A potential is applied between the rod 36 and the surface 37 with the rod 36 having a positive potential. A small current is passed between the rod 36 and the surface 37. At periods, the current may be reversed for a short time period, in order to clean the rod 36 from contaminants. The rod 36 may be made from a metallic material, such as titanium, which is compatible with the body fluid, such as blood. The current may alternatively be an alternating current, in order to influence upon the electrophoretic properties of the molecules. Also gradient electrical fields can be used, for example for dipole separation situations.

The embodiments described above may be used together with conventional dialysis as a supplement. One example would be a method comparable to diafiltration, employing both dialysis by diffusion and filtration.

Figure 5:
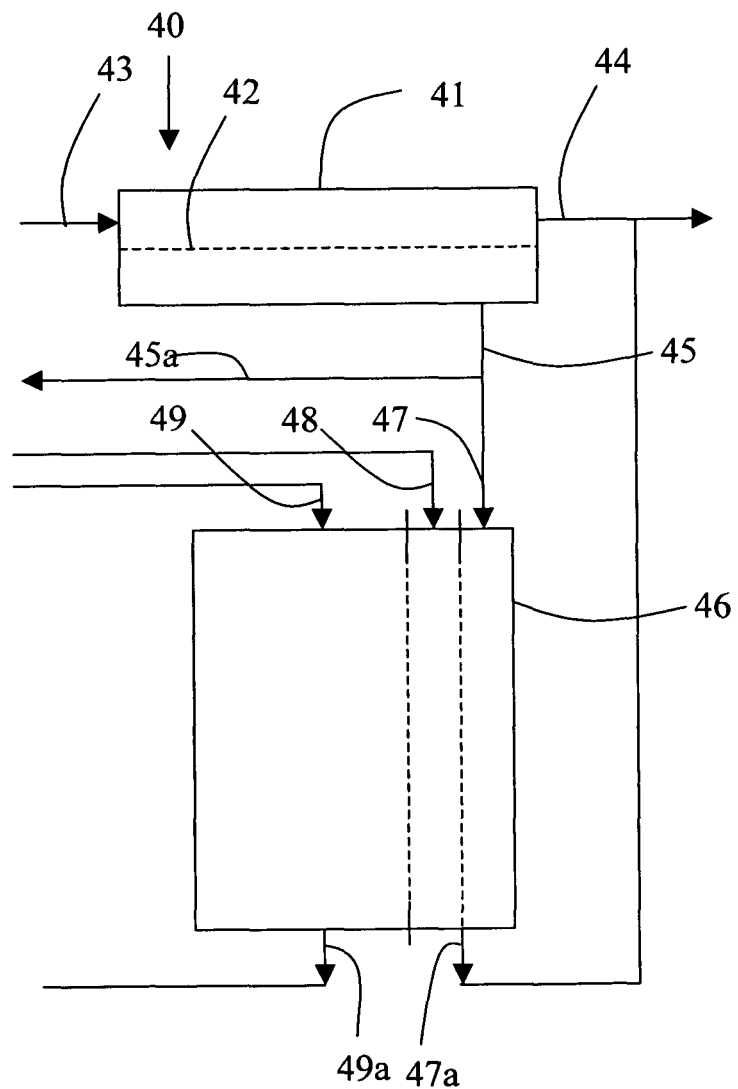
FIG. 5 is a schematic cross-sectional view of a diafiltration system according to a further embodiment of the invention.

In a fourth embodiment, shown in FIG. 5, the blood may be filtered in a first stage wherein the blood is passed through a conventional filtration membrane. Then, the filtrate can be exposed to the diffusion method according to the above embodiments. The filtrate having small solutes removed by the compartment 46 can be returned to the patient together with the retentate.

A conventional blood filter 40 comprises a compartment 41 having a filtration membrane 42. Blood is introduced into the compartment 41 via an inlet 43 and the retentate is returned to the body via outlet 44. A filtrate is removed from the filtration side of the membrane via outlet 45. The filter membrane is designed to pass molecules smaller than albumin, for example by having a pore size smaller than about 5 nm. A portion of the filtrate is removed to a waste via outlet 45a. The rest of the filtrate is passed to a diffusion unit according to any of the embodiments such as compartment 46, which comprises a filtrate inlet 47, a sterile fluid inlet 48 and a dialysis fluid inlet 49. At the other side of the compartment 46, there are a spent dialysis fluid outlet 49a and a body fluid outlet 47a, which is connected to the outlet 44 from the filter and returns the fluid to the body.

Several diffusion compartments 46 may be arranged in parallel in order to balance the size of the filtration device.

Below an examples of the flows are given: The blood flow at inlet 43 is 100 ml/min, and the outlet blood flow at outlet 44 is 45 ml/min. The filtered flow at outlet 45 is 55 ml/min. About half of that flow 30 ml/min is removed via outlet 45a and 25 ml/min is passed to inlet 47 of the diffusion compartment. Pure sterile water is delivered via inlet 48 to the transition zone at a flow rate of 25 ml/min. Dialysis fluid is delivered via inlet port 49 at a fluid flow rate compatible with the filtrate flow and the transition flow, in this example 100 ml/min. Such flows may be obtained by 200 parallel diffusion compartments 46. Thus, a body fluid flow of 50 ml/min is returned to the patient via outlet 47a. The total flow returned to the patient is 95 ml/min, resulting a net fluid removal of 5 ml/min from the patient. A flow of 30 ml/min of plasma is removed and discarded, which means that there is removed a relatively large amount of middle molecules, which pass the filtration membrane by convention. Since the body fluid comprises no, or only small amount of albumin, the diffusion compartment 46 may be made longer than in the examples given above, thereby improving the removal of creatinine.

The flows can have other values, which are desired under the circumstances. The membrane filter can be optimized for filtering out albumin and molecules and particles having larger diameter.

A further method of using the embodiment of FIG. 5 would be as shown in FIG. 6. The filter membrane 52 of filter compartment 51 may be designed with a pore size in the area of about 10 nm, whereby albumin would pass, but cellular bodies, bacteria, virus and large proteins would be retained.

The filter 50 may comprise a second filter membrane 53 being a nano-membrane having a pore size below 1 nm. The filtrate passing the first filter 52 is removed from the filter compartment 51 via outlet 54 and delivered to a diffusion compartment 56 as in the embodiment of FIG. 5. In this case, the body fluid also comprises albumin and other proteins. Via another outlet 55, the filtrate passing the nano-filter membrane 53 is removed and discarded. This discarded fluid mainly comprises water and small solutes, such as sodium and potassium.

The body fluid from outlet 54 enters the diffusion compartment 56 via inlet 57, while sterile fluid enters via inlet 58 and dialysis fluid via inlet 59. Spent dialysis fluid exits via a third outlet 59a and is discarded. The fluid, which is opposite, the sterile fluid inlet 58 exits via a second outlet 58a. The second outlet fluid comprises mainly molecules that have diffused out of the body fluid, such as small solutes, while comprising almost no middle molecules. This second outlet flow is returned directly to the patient. The fluid which is opposite the body fluid inlet 57 exits via a first outlet 57a. The body fluid from outlet 57a is delivered to a second diffusion compartment 61, which is considerably longer than the previous embodiments. The compartment 61 is so long that albumin has sufficient time to diffuse over the entire fluid flow so that albumin is equally distributed at the outlet of the compartment. The length is not shown in scale in FIG. 6 but should be substantially longer. The body fluid enters via inlet 62 and dialysis fluid enters via inlets 63 and 64. At the outlet portion, there is a narrow outlet 65 at the center and the rest of the fluid flow is returned to the patient via outlets 66 and 67.

The second diffusion compartment 61 can be said to operate as a reverse diffusion compartment. The molecules having a diffusion coefficient smaller than albumin will pass in the middle of the compartment to the outlet 65, while albumin and other smaller molecules will be equally distributed.

The following flows may be given as an example. The body fluid flow at the inlet 62 may be 0.125 ml/min and having a height (or rather width) of 10 μm. The inlets 63 and 64 may have a height of each 20 μm, and having a inlet flow of each 0.25 ml/min. The flow rate via outlet 65 may be 0.031 ml/min and having a height of about 2.5 μm. The outlets 66 and 67 may have a flow rate of each 0.297 ml/min and having a height of about 23.75 μm. This will give a total loss of albumin of 5% while the other middle molecules, which have a diffusion coefficient much smaller than albumin, are removed by 25%. A sufficient number of compartments are connected in parallel to achieve the desired total flow.

One example of the total flows is given below. The inlet flow to the filter is 100 ml/min. The retentate outlet flow is 40 ml/min. The filtrate passing the first micro-filter 52 is 60 ml/min. The body fluid flow via outlet 54 is 10 ml/min. The fluid flow passing the second filter 53 is 50 ml/min, which is discarded via outlet 55. The body fluid flow via outlet 54 enters the first diffusion compartment at inlet 57 and is 10 ml/min. Sterile pure water enters the first diffusion compartment at inlet 58 at a rate of 10 ml/min. The body fluid in the transition layer, which comprises mainly albumin and smaller molecules is delivered directly to the body via second outlet 58a at a flow rate of 10 ml/min. The body fluid in the first layer is delivered to the second reverse diffusion compartment 61 via inlet 62 at a flow rate of 10 ml/min. Dialysis fluid is entered at inlets 63 and 64 at a flow rate of each 20 ml/min in order to dilute the body fluid in the first layer by 1:5. The flow rate at outlet 65 is 5 ml/min and the flow rates at outlets 66 and 67 are 22.5 ml/min each. Thus, flow rates of 40 ml/min plus 10 ml/min, plus 22.5 ml/min plus 25 ml/min, in total 95 ml/min is returned to the patient. This embodiment can be optimized with other flows in order to further take advantage of the reverse diffusion compartment.

The above-mentioned embodiments may be used on whole blood or plasma or peritoneal dialysis fluid in order to remove certain molecules by diffusion.

Another method which does not require membranes are described below and it is called Field-Flow-Fractionation (FFF).

Basically, the FFF method applies an electrical field across a liquid flow channel and achieves separation from the combination of electrophoretic constants and flow resistance of different substances with the channel flow velocity profile. A random input mixture of substances will come out as an ordered sequence of substances. Alternatively, different substances will be guided into one or the other of two channel outlets in a continuous process.

A further method which does not require a membrane is the so-called antigen-antibody match type adsorption. The antigen-antibody type of absorption permits the exact selection of the substances to be eliminated out of the blood.

Figure 7:
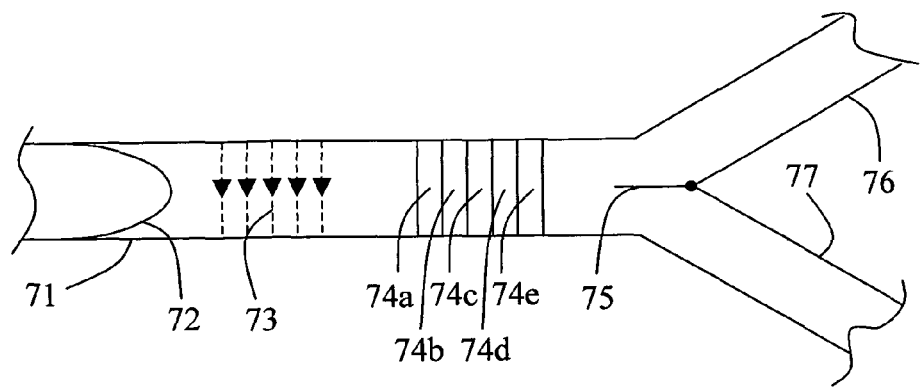
FIG. 7 is a schematic cross-sectional view of a FFF system according to a further embodiment of the invention.

FIG. 7 gives an overview of an analytic dialysis system. Based on a combination of the electrophoretic constant of a substance, an electric field 72 across the micro-channel and a liquid flow velocity profile 73 across the micro-channel 71, a chaotic input mixture of different substances is transformed into a sequential and ordered output of the different substances 74a, 74b, 74c, 74d, 74e. A flow switch 75 selects if the fluid flow of substances should pass into a first outlet 76 to be returned to the patient, or to a second outlet 77 to a waste in order to be discarded.

However, for the complete separation of a large number of substances, it could be desirable, due to e.g. small differences in the electrophoretic constants for some of the substances, to perform the complete separation in a number of series stages—each with e.g. different electrical field settings or different micro-channel geometry.

Figure 8:
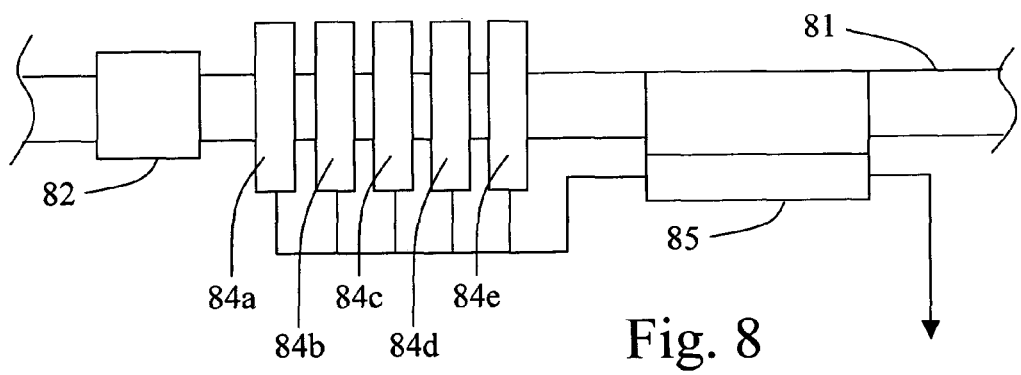
FIG. 8 is a schematic cross-sectional view of an analytic system according to a still further embodiment of the invention.

This situation is depicted in FIG. 8 in which also the below described osmotic water extraction is shown as an alternative to analytic water extraction. An blood flow turbine electrogenerator 82 provides electric power to several analytic separation cells 84a, 84b, 84c, 84d, 84e. The eliminated substances from the separation cells are provided to an osmotic water extration unit 85 for elimination of water from the main flow 81 which is then returned to the patient.

The liquid or body fluid acted upon may be blood taken out from a patient in an extracorporeal path, or inside the body. The liquid may alternatively be plasma having blood cells and other large particles removed. Still alternatively, the liquid may be peritoneal dialysis liquid, which is removed from the peritoneal cavity and cleaned for reuse. Yet alternatively, the liquid may be any other body fluid, such as interstitial fluid. The method may be used for the treatment of the body, such as by hemodialysis or peritoneal dialysis, or for analysis of substances in dialysate or any body fluid, or for diagnostic purpose.

By using magnetic nano-particles as carriers for the antigen agents in combination with applied magnetic control fields an enhanced absorption as well as cleaning process could be achieved by the utilization of separation, agitation, transportation and geometrical lock-in effects individually or in combinations.

Figure 9:
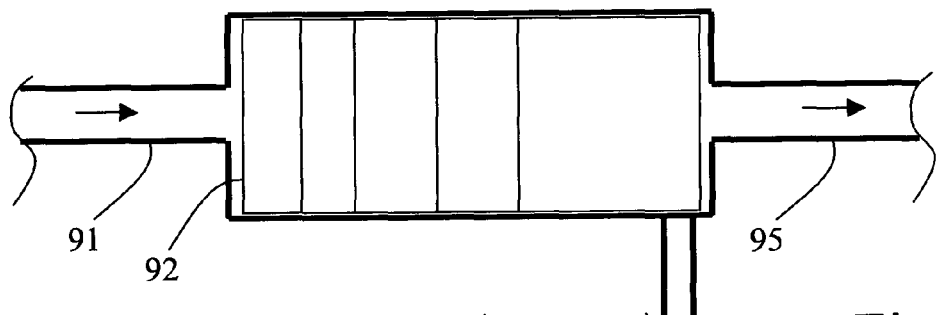
FIG. 9 is a schematic cross-sectional view of an absorption system according to a yet further embodiment of the invention.
Figure 10:
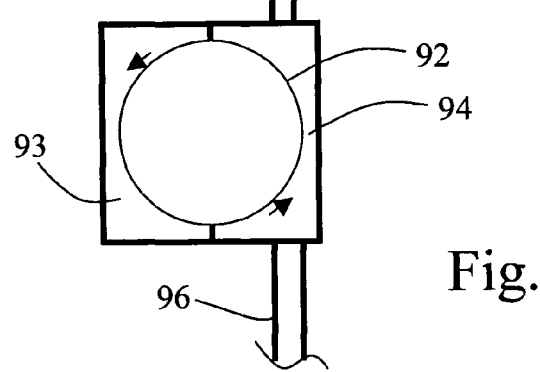
FIG. 10 is a transversal view of the system according to FIG. 9.

FIGS. 9 and 10 depict an embodiment of the invention using a high cycle rate continuous process rotating cylinder 92 to cycle the absorbing surface, or set of surfaces 94a, 94b, 94c, 94d, 94e, between absorbing and cleaning phases in an absorption chamber 93 and a cleaning chamber 94. Blood passing via an inlet 91 to the absorption chamber 93, wherein substances are removed from the blood via surfaces 94*a* to 94*e* and passes further on via an outlet 95 to the patient. An inlet 96 enters a cleaning fluid to the cleaning chamber 94 and the substances removed from the blood are eluted from the absorbing surfaces and exits via outlet 96.

Figure 11:
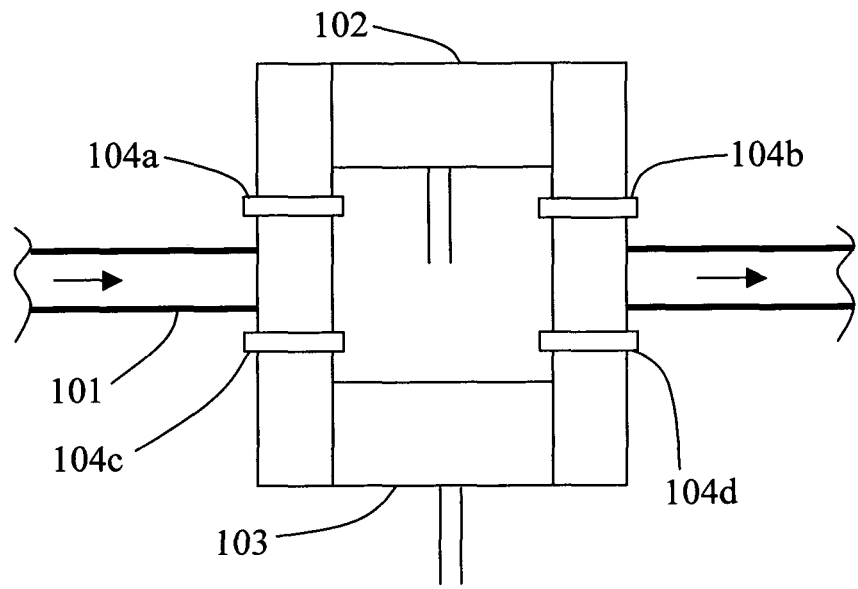
FIG. 11 is a schematic cross-sectional view of an alternating flow paths system according to still another embodiment of the invention.
Figure 12:
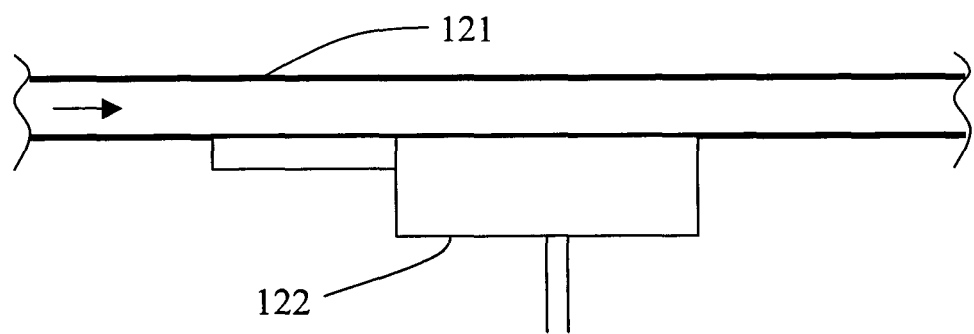
FIG. 12 is a schematic cross-sectional view of a system comprising water extraction function according to yet another embodiment of the invention.

FIG. 11 shows an alternative embodiment using high surface area low volume nano-particles. The blood from inlet 101 alternates between two flow paths 102, 103 via flow valves 104*a*, 104*b*, 104*c*, 104*d*. While one flow path 102 is conducting the blood flow the other flow path 103 is being cleaned.

A further embodiment performs extraction of water out of the blood stream. An analytic elimination principle would be employed. A benefit of the analytic method is that no membranes are involved. Alternatively, however, a semi-permeable membrane and osmotic pressure could be used. To create a positive osmotic pressure between the blood and the artificial urine drain vessel, the high eliminated waste products concentration is used to draw water from the blood path 121 into the urine drain vessel 122. This procedure is depicted in FIG. 11.

The invention claimed is:

1. A method for differentiation of substances in a body fluid, comprising entering the body fluid, a transition fluid and a diffusion fluid via inlets into a compartment for flowing parallel with each other in laminar flow layers with substantially equal flow velocities, whereby the transition fluid layer is interposed between the body fluid layer and the diffusion fluid layer;

removing the body fluid and at least a portion of the transition fluid via a first outlet and removing at least the diffusion fluid via a second outlet from the compartment;

adjusting the flow velocities so that a marker substance will not diffuse across the transition layer, during the passage from an inlet to an outlet of the compartment;

whereby the transition fluid is sterile.

2. The method according to claim 1, whereby the marker substance is albumin.

3. The method according to claim 1, whereby substances in the body fluid having a larger diffusion velocity than the marker substance diffuse into the diffusion fluid.

4. The method according to claim 1, whereby the transition fluid and the diffusion fluid are the same fluid, which is dialysis liquid for hemodialysis.

5. The method according to claim 1, wherein the diffusion fluid is non-sterile.

6. The method according to claim 1, wherein the sterile transition fluid is sterile water.

* * * * *